United States Patent [19]

Rudin

[11] E Patent Number: Re. 32,811

[45] Reissued Date of Patent: Dec. 27, 1988

[54] EASILY DISPERSIBLE DIETARY FIBER PRODUCT AND METHOD FOR PRODUCING THE SAME

[75] Inventor: Richard E. Rudin, Kenosha, Wis.

[73] Assignee: S. C. Johnson & Son, Inc., Racine, Wis.

[21] Appl. No.: 870,245

[22] Filed: Jun. 3, 1986

Related U.S. Patent Documents

Reissue of:

[64] Patent No.: 4,551,331
Issued: Nov. 5, 1985
Appl. No.: 500,603
Filed: Jun. 2, 1983

[51] Int. Cl.[4] ..... A61K 35/78

[52] U.S. Cl. ..... 424/195.1

[58] Field of Search ..... 424/198.1; 514/892

[56] References Cited

U.S. PATENT DOCUMENTS

| | | | |
|---|---|---|---|
| 1,891,697 | 12/1932 | Tuvin | 424/442 |
| 2,043,204 | 6/1936 | Spalding | 167/56 |
| 2,060,336 | 11/1936 | Near et al. | 99/131 |
| 2,090,537 | 8/1937 | Lund | 260/99.2 |
| 2,095,259 | 10/1937 | Kober et al. | 167/56 |
| 2,132,484 | 10/1938 | Kober | 209/172 |
| 2,146,867 | 2/1939 | Welin | 167/82 |
| 2,278,464 | 4/1942 | Musher | 167/56 |
| 2,540,253 | 2/1951 | Gakenheimer | 167/57 |
| 2,554,143 | 5/1951 | Hinz et al. | 99/139 |
| 2,613,150 | 10/1952 | Halden | 99/139 |
| 2,749,244 | 6/1956 | Winner | 99/139 |
| 2,819,970 | 1/1958 | Steigmann | 99/130 |
| 2,819,971 | 1/1958 | Gunthardt | 99/130 |
| 2,953,458 | 9/1960 | Sjoliema | 99/56 |
| 3,054,675 | 9/1962 | Hale et al. | 99/56 |
| 3,056,683 | 10/1962 | Cyr | 99/207 |
| 3,190,756 | 6/1965 | Aurell et al. | 99/90 |
| 3,202,578 | 8/1965 | Parker | 167/56 |
| 3,291,614 | 12/1966 | Tumerman | 99/56 |
| 3,560,218 | 2/1971 | Whelan | 99/26 |
| 3,893,842 | 7/1975 | Glabe et al. | 426/205 |
| 4,023,978 | 5/1977 | Messina | 106/213 |
| 4,143,163 | 3/1979 | Hutchinson et al. | 426/96 |
| 4,156,020 | 5/1979 | Bohrmann et al. | 426/96 |
| 4,198,400 | 4/1980 | Biegler | 424/180 |
| 4,215,152 | 7/1980 | O'Rourke | 426/579 |
| 4,219,580 | 8/1980 | Torres | 426/549 |
| 4,229,488 | 10/1980 | Suggs et al. | 426/557 |
| 4,260,642 | 4/1981 | Mitchell et al. | 426/579 |
| 4,310,557 | 1/1982 | Suggs et al. | 426/96 |
| 4,321,263 | 3/1982 | Powell et al. | 424/195 |
| 4,459,280 | 7/1984 | Colliopoulos et al. | 424/35 |
| 4,548,806 | 10/1985 | Colliopoulos et al. | 424/35 |

FOREIGN PATENT DOCUMENTS

| | | |
|---|---|---|
| 0105195 | 4/1984 | European Pat. Off. . |
| 56-0100722 | 8/1981 | Japan . |
| 756885 | 1/1957 | United Kingdom . |

OTHER PUBLICATIONS

Collection of Trade Literature on Coating Material Tested in Exhibit 10; Atmos 300, Myvatem 92, Tween ©80, 40-06S, (Myatex), Sterolac S, Soft Touch, 3-50 (Myvatex), Texture Lite, Myalet 50-7, EW-6, Crisco Oil, Tween ©40, Durem 300, Yelkin 300.

Durkee Shortenings & Oil Glossary, SCM Durkee Industrial Foods.

Rubber World, Aug. 1981, "Fluidized Bed Mixing of Dry Liquid Dispersions".

Myvatex Texture Lite Food Emulsifiers (k), Eastham Chemicals Publication No. ZM-65B, Sep. 1983.

A. G. Mattha, "Rheology of Dispersions of Macromolecular Substances. Part 8. Rheological Studies on Plantago albicans (Psyllium) Seed Gum Dispersions. II. Effect of Some Pharmaceutical Additives." *Pharm. Acta Helv.* 52(9): 214-217 (1977).

A. G. Mattha, "Rheology of Dispersions of Macromolecular Substances" Part 7. Rheological Studies on Plantago albicans (Pysllium) Seed Gum Dispersions. I. General Flow Characteristics. *Pharma. Acta Helv.* 52(9): 210-213 (1977).

A. G. Mattha, "Influence of Some Pharmaceutical Adjuvants on the Syneresis of Plantago albicans (Pysllium) Seed Gum Gels." *Pharm. Acta Helv.* 52 (10): 233-235 (1977).

L. Carino and H. Mollet, "Wetting of a Powder by Aqueous Solutions of Surface Active Agents". *Powder Technology*, 11: 189-194 (1975).

*Primary Examiner*—Anton H. Sutto

[57] ABSTRACT

A modified dry dietary fiber product which is readily dispersible in liquids such as water, comprises a dry dietary fiber product coated with from 0.5 to 20% by weight of the food grade emulsifier. Process for producing coated dietary fiber products comprises blending these dietary fiber product materials with the mixture of a non-toxic solvent in a food grade emulsifier followed by removing the solvent.

* * * * *

The questions raised in reexamination request No. 90/001,032, filed May 22, 1986, have been considered and the results thereof are reflected in this reissue patent which constitutes the reexamination certificate required by 35 U.S.C. 307 as provided in 37 CFR 1.570(e).

36 Claims, No Drawings

EASILY DISPERSIBLE DIETARY FIBER PRODUCT AND METHOD FOR PRODUCING THE SAME

Matter enclosed in heavy brackets [ ] appears in the original patent but forms no part of this reissue specification; matter printed in italics indicates the additions made by reissue.

BACKGROUND

This invention relates to modified dietary fiber products and processes for producing the same. More particularly, this invention relates to modified dietary fiber products such as bulk laxatives which are readily and easily dispersible in water and other liquids.

Dietary fibers such as psyllium powder, bran, cellulose derivatives such as sodium carboxymethyl cellulose, malt extract, wheat germ and the like have long been used as dietary supplements. These materials generally are relatively fine powders or particles which resist wetting due to their very dry nature. The most important of these dietary fibers materials are psyllium and bran. Psyllium powder may be derived from the ground husks of the seeds of plantago ovata, plantago psyllium or plantago indica. The laxative properties to this material are due to its hydrophillic properties and to its mucilaginous character when wetted. Bran has similar characteristics.

Historically, dry bulk laxative composition contain bulking agents such as psyllium powder and a large percentage of sugar, usually dextrose, as a dispersing agent. Some flavored bulk laxatives contain as much as 70% sugar. These dietary fiber compositions are added to water by the user to produce a dispersion of the powder. The powder picks up the moisture from this dispersion to become mucilaginous. However, even after vigorous agitation, a substantial amount of time is required for complete dispersal and miscibility of the bulking agent and the sugar in an aqueous system.

Many attempts have been made to overcome the dispersal problems of dry dietary fiber products such as bulk laxatives, specifically those including psyllium. One method of improving the dispersibility of psyllium powder is by using a psyllium having a wide range of particle sizes. It has been suggested that the different particle sizes are more dispersible than a product having a uniform particle size which is normally sold to produce formulators. However, these materials are not sufficiently more dispersible than standard substantially uniform particle size psyllium preparations.

A second method of improving the dispersibility of psyllium is disclosed in U.S. Pat. No. 4,321,263. This patent discloses coating or granulating the psyllium with polyvinylpyrrolidone as a granulating agent and polyethylene glycol as a dispersing agent. As disclosed in this patent, the polyvinylpyrrolidone also functions to reduce the friability of the resulting psyllium granules.

Still other attempts to improve the dispersibility of bulk fibers, specifically psyllium, are known which utilize an effervescent sugar-psyllium mixture to achieve the dispersal of the psyllium by the physical action of the carbon dioxide released when the product is added to water. These products, however, often contain high quantities of sodium ions as well as sugar and therefore cannot be safely used by patients whose intake of sugar or sodium is restricted.

BRIEF DESCRIPTION AND OBJECTS OF THE INVENTION

It has been surprisingly found that dietary fiber products can be coated with a small amount of an ingestible food grade emulsifier to produce a modified dietary fiber which is readily and easily dispersible in liquids. The method of coating the dietary fibers comprises mixing the dietary fiber with a small percentage of a food grade emulsifier dissolved in a non-toxic solvent for the emulsifier and removing the solvent.

It is therefore the primary object of the present invention to provide a dry dietary fiber product which is easily and readily dispersible in liquids.

It is a further object of the present invention to provide a process for preparing these quickly dispersible dietary fiber products.

It is a still further object of the present invention to provide a dietary fiber product which need not contain sugar, phosphorous, sodium or potassium ions.

It is a still further object of the present invention to provide a method for coating a variety of dietary fiber products such that dispersible sugar free products can be produced.

It is a still further object of the present invention to provide a dietary fiber product having a coating of food grade emulsifier.

It is a still further object of the present invention to provide a readily dispersible bulk laxative product.

It is a still further object of the present invention to provide a modified psyllium laxative product.

Still further objects and advantages of the product and process of the present invention will become more apparent from the following detailed description thereof.

DETAILED DESCRIPTION OF THE INVENTION

As used in the instant specification and claims the term "dietary fiber" means edible seeds and/or grains, especially the husks and/or germ of these seeds. Dietary fibers are used as bulk laxatives and as food supplements.

The present invention relates primarily to a modified dietary fiber materials. This product comprises from about 80 to 99.95% by weight of at least one dietary fiber and from about 0.05 to 20% by weight of a food grade emulsifier; wherein the emulsifier substantially coats the fiber to prevent agglomeration when added to liquids.

The present invention also relates to a process for preparing the above coated fiber materials. One embodiment of this process comprises mixing at least one dietary fiber with a mixture of from about 0.5 to 20% by weight of a food grade emulsifier and from about 0.5 to 40% by weight of a non-toxic solvent; and removing the solvent to form a dry free flowing product.

The present invention relates to modified dietary fiber products and methods for modifying these materials. Dietary fibers are useful as bulk forming laxatives. These materials are well known in the over-the-counter drug business. It is also well known that dietary fibers such as bulk laxatives, in their pure form resist wetting, agglomerate when mixed with liquids and do not disperse as a homogenous mixture. Examples of dietary fiber materials suitable for use in the compositions and methods of the present invention include psyllium preparations such as plantago seeds, i.e., plantago ovata, plantago psyllium, plantago indica, etc., plantago ovata husks, the hemicellulose of psyllium, psyllium seed, blond psyllium seed, psyllium seed husks, bran, wheat germ and mixtures thereof. By the term "bran" is meant the seed husk from any of a number of cereal grains including wheat, rice, rye, oats, barley, corn and mixtures thereof.

The dietary fiber should be present in the final composition of the present invention in an amount of from about 80 to 99.95% by weight. The fiber can be present either as a single material or as combinations of different psyllium preparations, bran, cereal germ and combinations of these materials. It is preferred that the final product contain from about 90 to 99.95% by weight dietary fiber and it is most preferred that the final product contain from about 95 to 99.95% by weight of these materials. Furthermore, when mixtures of psyllium and other materials such as bran are used, the total dietary fiber present in the formulation should contain from about 30 to 99% by weight psyllium and from about 70 to 1% by weight other fiberous material.

The composition of the present invention also includes from about 0.05 to 20% by weight of the food grade emulsifier. Suitable emulsifiers include MYVATEX Texture Lite Emulsifier available from Eastman Kodak, Health and Nutrition Division, Kingsport, Tenn. This material is a mixture of distilled propylene glycol monoglycerides, distilled monoglycerides and sodium stearoyl lactylate. Other emulsifiers also can be used including hydrophilic ethoxylated sorbitan monoesters such as the Tweens available from ICI America, especially sorbitan monostearate plus 20 moles of ethylene oxide (Tween 60), sorbitan mono-oleate plus 20 moles of ethylene oxide (Tween 80) and the like, malto dextran, lecithin, monoglycerides of food grade quality formed of fatty acids having a carbon chain length of between $C_4$ and $C_{24}$, diglycerides of food grade quality formed from fatty acids having a carbon content of between $C_4$ and $C_{24}$, vegetable oil, and mixtures thereof. The preferred emulsifier is the sorbitan monostearate plus 20 moles of ethylene oxide. The emulsifier should be present in the composition of the present invention in the amount of from about 0.05 to 20% by weight. Preferably, the composition should include from about 0.05 to 10% and optionally from about 0.05 to 5% by weight.

As noted above, it was most surprising that coating the dietary fibers with the thin coating of the above described emulsifiers causes the fibers to resist agglomeration when they are added to a liquid such as water. Instead of a agglomerating, the particles of the dietary fiber disperse without lumping or aggregation. The liquid permeates each particle and causes the particular fibrous material to disperse uniformly and homogeneously. Minimal stirring of the fiber into the liquid is required as compared with other products currently available in the marketplace which require vigorous stirring, shaking or even a mechanical blending to break up agglomerations of large masses of unwetted particles.

It is thought the thin coating by the food grade emulsifier temporarily retards the hydration and the resultant swelling of the dietary fiber product, allowing ample time for the consumer to ingest the product. Existing psyllium type products require that the mixture be consumed almost instantly after mixing. If the prior art mixtures are allowed to stand even for a short period of time the products become so mucilagenous and thick that it is difficult to swallow them.

One method for producing the modified dietary fibers of the present invention is by mixing the fibrous material with a mixture of an emulsifier and a non-toxic solvent. The dietary fiber should be mixed from about 0.05 to 20% of a food grade emulsifier and mixed with from 0.5 to 40% by weight of a solvent. Suitable solvents include water, ethanol, mixtures of water and ethanol, mixtures of water, ethanol and ethyl acetate whereby the ethyl acetate is present in small quantities such as denatured ethyl alcohol. The solvent, emulsifier and dietary fiber are than mixed so that the emulsifier coats the dietary fiber.

The mixing can be done using any of a number of different conventional mixing processes so long as intimate contact between the emulsifier and the dietary fiber is achieved. Examples of such processes include the Wurster process which is a modified fluid bed coating system for producing encapsulated products. A second process is the Durkee encapsulation process which is essentially an air suspension coating process, i.e., the fluidized bed is supported with air and sprayed with a coating material. A third type of process includes use of a Littleford blender of the type described in the August, 1981 "Rubber World" article entitled "Fluidized Bed Mixing of Dry Liquid Dispersions". Other suitable mixers include the Twin Shell mixer (PK blender) and cone mixers such as the Nauda mixer from The Day Company.

After the solvent, emulsifier and dietary fiber are mixed together, the solvent is flashed off using conventional means to form the coated dry fiber product. Still a further method of blending the emulsifier with the dietary fiber is to use the Littleford/Logie Blender without using any solvent. Heat may also be applied to the mixture to speed up the coating process but is not essential.

In addition, the compositions of the present invention can include other ingredients to improve the palatability or flavor of the composition. In this regard, citric acid or other acids may be added to the composition to impart tartness or other flavor characteristics. If acids are utilized, suitable pH buffering agents also may be utilized such as mono-calcium phosphate monohydrate, sodium citrate, etc. Obviously, the incorporation of these buffering materials should be avoided if the product is intended to be used by persons on a low sodium or phosphate diet. Also, sweetening agents and/or flavoring materials can be included. Suitable sweetening agents include sucrose, dextrose, fructose and other sugars as well as artificial sweetening agents such as saccerin, cyclamates and aspartame, i.e., N-L-Alpha-Aspartyl-L-Phenylalamine-1-Methyl ester. Also suitable food grade coloring agents also may be included.

The composition and method of the present invention will now be illustrated by way of the following examples which are for the purposes of illustration and are not in any way to be considered as limiting. In the following examples, all parts and percentages are by weight and all temperatures are in degrees Celsius.

EXAMPLE 1

86.67 grams of pure ethyl alcohol was mixed with 13.33 grams of sorbitan monostearate plus 20 moles of ethylene oxide (polysorbate 60-Tween 60). To a Littleford/Logie blender was added 70 grams of 40 mesh psyllium and 29.60 grams of bran. Also, three grams of the ethyl alcohol-polysorbate 60 mixture was added and the entire mixture was blended together to uniformity and until all the bran and psyllium particles were wetted. At this time the solvent was removed by air drying to produce a coated psyllium bran mixture having the following percent composition.

| | |
|---|---|
| Psyllium | 70.0% |
| Bran | 29.6% |
| Polysorbate 60 | 0.4% |

When 5.0 grams of this product was added to 8 ounces (236 ml) of water, the material quickly dispersed with simple mixing.

EXAMPLE 2

The procedure of Example 1 was repeated with the exception that the bran was replaced by the various brans such as red wheat bran, white wheat bran, oat bran, corn bran and rice bran. Both natural and roasted brans were used. In each case, similar results to those observed in Example 1 were obtained.

EXAMPLE 3

The procedure of Example 1 was repeated with the exception that the particle size of the bran was varied from exceptionally fine particles having a particle size less than 106 microns through large particle flakes (2,000 microns). In each instance similar results to those obtained in Example 1 were observed.

EXAMPLE 4

A series of coated dietary fibers were prepared using the procedure of Example 1. These dietary fibers have the final formulation as set forth in Example 1. In each case, either ethyl alcohol or SDA 35 denatured ethyl alcohol were utilized as the solvent:

TABLE I

| Component/ Run | A | B | C | D | E | F | G | H |
|---|---|---|---|---|---|---|---|---|
| Psyllium Powder (40 Mesh) | 99.70 | 99.80 | 99.66 | 70.00 | 99.70 | — | — | — |
| Bran (425 microns) | — | — | — | 29.70 | — | — | — | — |
| Wheat Bran (180 microns) | — | — | — | — | — | 99.60 | — | — |
| Corn Bran (250 microns) | — | — | — | — | — | — | 99.60 | — |
| Wheat Germ (425 microns) | — | — | — | — | — | — | — | 99.60 |
| Polysorbate 60[1] | 0.30 | — | 0.23 | — | — | 0.40 | 0.40 | 0.40 |
| Polysorbate 80[2] | — | 0.20 | — | — | — | — | — | — |
| Lecithin | — | — | — | 0.30 | — | — | — | — |
| Myvatex[3] | — | — | — | — | 0.30 | — | — | — |
| Vegetable Oil | — | — | 0.11 | — | — | — | — | — |

[1]Polysorbate 60 - Sorbitan monostearates plus 20 moles of ethylene oxide - Tween 60.

[2]Polysorbate 80 - Sorbitan monoleate plus 20 moles of ethylene oxide - Tween 80.

[3]Myvatex - Myvatex Texture Lite - a mixture of distilled propylene glycol monoglycerides, distilled monogylcerides and sodium stearoyl lactylate available from Eastman Kodak.

When added to water, each of these formulations were readily dispersed by simple hand mixing.

EXAMPLE 5

A flavored composition was prepared having the following formulation:

| | |
|---|---|
| Coated psyllium-bran mixture of Example 1 | 86.573% |
| Citric acid | 8.657% |
| Aspartame (Nutri-Sweet - G. D. Searle) | 0.693% |
| Orange flavor | 2.597% |
| FD and C yellow No. 6 Lake | 0.095% |
| Beta Carotene 1% CWS. | 1.385% |

This formulation, when added to water, was readily dispersed using simple stirring and remained drinkable for approximately 5 minutes. The formulation had a pleasing orange flavor with a hint of tartness.

EXAMPLE 6

A flavored composition was prepared having the following formulation:

| | |
|---|---|
| Coated bran of Example 4.A | 81.86% |
| Citric acid | 11.69% |
| Aspartame | 0.94% |
| Orange flavor | 3.51% |
| FD & C Yellow No. 6 Lake | 0.12% |
| Beta Carotene 1%, CWS | 1.88% |

This formulation was a free flowing powder which was readily dispersible in water. The resulting composition remained in a drinkable consistency for at least 5 minutes and had a pleasing orange flavor with some tartness.

EXAMPLE 7

A flavored composition was prepared having the following formulation:

| | |
|---|---|
| Coated bran of Example 4.F | 81.86% |
| Citric acid | 11.69% |
| Aspartame | 0.94% |
| Orange flavor | 3.51% |
| FD & C Yellow No. 6 Lake | 0.12% |
| Beta Carotene 1%, CWS | 1.88% |

This formulation was a free flowing powder which was readily dispersible in water. The resulting composition remained in a drinkable consistency for at least 5 minutes and had a pleasing orange flavor with some tartness.

What I claim is:

1. A coated dietary fiber which is readily dispersible in liquids without agglomeration [comprising] *consisting essentially of* from about 80 to 99.95% by weight of at least one dietary fiber *having laxative properties and* subject to agglomeration upon mixing with liquids, and from about 0.05 to 20% by weight of a food grade emulsifier wherein the emulsifier substantially coats the powder to prevent agglomeration when added to liquids.

2. The composition of claim 1 wherein the dietary fiber is selected from the group consisting of psyllium, dietary bran, wheat germ and mixtures thereof.

3. The composition of claim 2 wherein the emulsifier is selected from the group consisting of a mixture of distilled propylene glycol monoglycerides, distilled monoglycerides and sodium stearyl lactylate hydrophylic ethoxylated sorbitan monoesters, malto dextran, lecithin, monoglycerides, diglycerides, and mixtures thereof.

4. The composition of claim 3 wherein the composition comprises from about 90 to 99.95% by weight dietary fiber, and from 0.05 to 10% by weight emulsifier.

5. The composition of claim 1 wherein the emulsifier is selected from the group consisting of a mixture of distilled propylene glycol monoglycerides, distilled monoglycerides and sodium stearyl lactylate hydrophyllic ethoxylated sorbitan monoesters, malto dextran, lecithin, monoglycerides, diglycerides, and mixtures thereof.

6. The composition of claim 5 wherein the hydrophyllic ethoxylated sorbitan monoesters are selected from the group consisting of sorbitan monostearate plus 20 moles of ethylene oxide, soriban monoleate plus 20 moles of ethylene oxide and mixtures therein.

7. The composition of claim 1 wherein the composition comprises from about 90 to 99.95% by weight dietary fiber, and from 0.05 to 10% by weight emulsifier.

8. The composition of claim 1 wherein said dietary fiber is a mixture of psyllium, cellulose derivatives and cereal bran.

9. The composition of claim 8 wherein said mixture comprises from 30 to 99% by weight psyllium and from 1 to 70% by weight bran.

10. The composition of claim 1 wherein the composition comprises from about 95 to 99.95% by weight dietary fiber and from about 0.05 to 5% by weight of the emulsifer.

11. The composition of claim 1 wherein the emulsifier is sorbitan monostearate plus 20 moles of ethylene oxide.

12. A process for producing a modified dietary fiber which [comprises] *consists essentially of* mixing a dietary fiber *having laxative properties and* subject to agglomeration upon mixing with liquids, with about 0.05 to 20% by weight of [an] *a food grade* emulsifier and about 0.5 to 40% of a non-toxic solvent; and removing the solvent to form a dry, free-flowing product.

13. The process of claim 12 wherein the dietary fiber is selected from the group consisting of psyllium, dietary bran, wheat germ, and mixtures thereof.

14. The process of claim 12 wherein the emulsifier is selected from the group consisting of a mixture of distilled propylene glycol monoglycerides, distilled monoglycerides and sodium stearyl lactylate, hydrophylic ethoxylated sorbitan monoesters, malto dextran, lecithin, monoglycerides, diglycerides, and mixtures thereof.

15. The process of claim 12 wherein the dietary fiber is a mixture of psyllium, cellulose derivatives and cereal bran.

16. The process of claim 15 wherein said mixture comprises from 99 to 30% by weight psyllium and 1 to 70% by weight bran.

17. The process of claim 14 wherein the hydrophyllic ethoxylated sorbitan monoesters are selected from the group consisting of sorbitan monoleate plus 20 moles of ethylene oxide, sorbitan monostearate plus 20 moles of ethylene oxide and mixtures thereof.

18. The process of claim 12 wherein the emulsifier is sorbitan monostearate plus 20 moles of ethylene oxide.

19. The process of claim 12 wherein the emulsifier is present in an amount of from 0.05 to 10% by weight.

20. The process of claim 12 wherein the solvent is selected from the group consisting of ethyl alcohol, water, mixtures of ethyl alcohol and ethyl acetate and mixtures thereof.

21. A coated dietary fiber which is readily dispersible in liquids without agglomeration [comprising] *consisting essentially of* from about 80 to 99.95% by weight of psyllium *having laxative properties,* and from about 0.05 to 20% by weight of a mixture of distilled propylene glycol monoglycerides, distilled monoglycerides and sodium stearyl lactylate, wherein said mixture substantially coats the psyllium to prevent agglomeration when added to liquids.

*22. A coated dietary fiber which is readily dispersible in liquids without agglomeration consisting essentially of from about 80 to 99.5% by weight of psyllium having laxative properties, and from about 0.05 to 20% by weight of sorbitan monostearate plus 20 moles of ethylene oxide, wherein said sorbitan monostearate plus 20 moles of ethylene oxide substantially coats the psyllium to prevent agglomeration when added to liquids.*

*23. A coated dietary fiber which is readily dispersible in liquids without agglomeration consisting essentially of from about 80 to 99.5% by weight of psyllium having laxative properties, and from about 0.05 to 20% by weight of sorbitan monooleate plus 20 moles of ethylene oxide, wherein said sorbitan monooleate plus 20 moles of ethylene oxide substantially coats the psyllium to prevent agglomeration when added to liquids.*

*24. A coated dietary fiber which is readily dispersible in liquids without agglomeration consisting essentially of from about 80 to 99.5% by weight of psyllium having laxative properties, and from about 0.05 to 20% by weight of lecithin, wherein said lecithin substantially coats the psyllium to prevent agglomeration when added to liquids.*

*25. A coated dietary fiber which is readily dispersible in liquids without agglomeration consisting essentially of from about 80 to 99.95% by weight of at least one dietary fiber having laxative properties and subject to agglomeration upon mixing with liquids, and from about 0.05 to 20% by weight of a food grade emulsifier selected from the group consisting of a mixture of distilled propylene glycol monoglycerides, distilled monoglycerides and sodium stearyl lactylate, hydrophilic ethoxylated sorbitan monoesters, lecithin, monoglycerides, diglycerides, and mixtures thereof, wherein the emulsifier substantially coats the fiber to prevent agglomeration when added to liquids.*

*26. A coated dietary fiber which is readily dispersible in liquids without agglomeration consisting essentially of from about 80 to 99.95% by weight of at least one dietary fiber having laxative properties and subject to agglomeration upon mixing with liquids, and from about 0.05 to 20% by weight of a food grade emulsifier which is at least one hydrophilic ethoxylated sorbitan monoester, wherein the emulsifier substantially coats the fiber to prevent agglomeration when added to liquids.*

*27. A coated dietary fiber which is readily dispersible in liquids without agglomeration consisting essentially of from about 80 to 99.95% by weight of at least one dietary fiber having laxative properties and subject to agglomeration upon mixing with liquids, and from about 0.05 to 20% by weight of a food grade emulsifier which is lecithin, wherein the emulsifier substantially coats the fiber to prevent agglomeration when added to liquids.*

*28. A coated dietary fiber which is readily dispersible in liquids without agglomeration consisting essentially of from about 80 to 99.95% by weight of at least one dietary fiber having laxative properties and subject to agglomeration*

*upon mixing with liquids, and from about 0.05 to 20% by weight of a food grade emulsifier selected from the group consisting of monoglycerides, diglycerides and mixtures thereof, wherein the emulsifier substantially coats the fiber to prevent agglomeration when added to liquids.*

*29. A coated dietary fiber which is readily dispersible in liquids without agglomeration consisting essentially of from about 80 to 99.95% by weight of at least one dietary fiber having laxative properties and subject to agglomeration upon mixing with liquids and selected from the group consisting of psyllium, bran, cellulose derivatives and mixtures thereof, and from about 0.05 to 20% by weight of a food grade emulsifier selected from the group consisting of a mixture of distilled propylene glycol monoglycerides, distilled monoglycerides and sodium stearyl lactylate, hydrophilic ethoxylated sorbitan monoesters, lecithin, monoglycerides, diglycerides, and mixtures thereof, wherein the emulsifier substantially coats the fiber to prevent agglomeration when added to liquids.*

*30. A coated dietary fiber which is readily dispersible in liquids without agglomeration consisting essentially of from about 80 to 99.95% by weight of at least one dietary fiber having laxative properties and subject to agglomeration upon mixing with liquids and selected from the group consisting of psyllium, bran, cellulose derivatives and mixtures thereof, and from about 0.05 to 20% by weight of a food grade emulsifier which is at least one hydrophilic ethoxylated sorbitan monoester, wherein the emulsifier substantially coats the fiber to prevent agglomeration when added to liquids.*

*31. A coated dietary fiber which is readily dispersible in liquids without agglomeration consisting essentially of from about 80 to 99.95% by weight of at least one dietary fiber having laxative properties and subject to agglomeration upon mixing with liquids and selected from the group consisting of psyllium, bran, cellulose derivatives and mixtures thereof, and from about 0.05 to 20% by weight of a food grade emulsifier which is lecithin, wherein the emulsifier substantially coats the fiber to prevent agglomeration when added to liquids.*

*32. A coated dietary fiber which is readily dispersible in liquids without agglomeration consisting essentially of from about 80 to 99.95% by weight of at least one dietary fiber having laxative properties and subject to agglomeration upon mixing with liquids and selected from the group consisting of psyllium, bran, cellulose derivatives and mixtures thereof, and from about 0.05 to 20% by weight of a food grade emulsifier selected from the group consisting of monoglycerides, diglycerides and mixtures thereof, wherein the emulsifier substantially coats the fiber to prevent agglomeration when added to liquids.*

*33. A coated dietary fiber which is readily dispersible in liquids without agglomeration consisting essentially of from about 80 to 99.95% by weight of psyllium having laxative properties, and from about 0.05 to 20% by weight of a food grade emulsifier selected from the group of consisting of a mixture of distilled propylene glycol monoglycerides, distilled monoglycerides and sodium stearyl lactylate, hydrophilic ethoxylated sorbitan monoesters, lecithin, monoglycerides, diglycerides, and mixtures thereof, wherein the emulsifier substantially coats the fiber to prevent agglomeration when added to liquids.*

*34. A coated dietary fiber which is readily dispersible in liquids without agglomeration consisting essentially of from about 80 to 99.95% by weight of psyllium having laxative properties, and from about 0.05 to 20% by weight of a food grade emulsifier which is at least one hydrophilic ethoxylated sorbitan monoester, wherein the emulsifier substantially coats the fiber to prevent agglomeration when added to liquids.*

*35. A coated dietary fiber which is readily dispersible in liquids without agglomeration consisting essentially of from about 80 to 99.95% by weight of psyllium having laxative properties, and from about 0.05 to 20% by weight of a food grade emulsifier selected from the group consisting of monoglycerides, diglycerides and mixtures thereof, wherein the emulsifier substantially coats the fiber to prevent agglomeration when added to liquids.*

*36. The coated dietary fiber according to anyone of claims 25–35, wherein the emulsifier is present from about 0.05 to 1.0% by weight.*

* * * * *